United States Patent [19]

Sarges

[11] Patent Number: 4,940,708

[45] Date of Patent: Jul. 10, 1990

[54] 4-ARYLSULFONYL-3,4-DIHYDRO-2(1H)-QUINOXALINONE-1-ALKANOIC ACIDS, ESTERS, AND SALTS

[75] Inventor: Reinhard Sarges, Mystic, Conn.

[73] Assignee: Pfizer Inc., New York, N.Y.

[21] Appl. No.: 424,298

[22] PCT Filed: Oct. 30, 1986

[86] PCT No.: PCT/US86/02335

§ 371 Date: Jun. 30, 1988

§ 102(e) Date: Jun. 30, 1988

[51] Int. Cl.$^5$ ................. C07D 241/50; A61K 31/495
[52] U.S. Cl. ..................................... 514/249; 544/354
[58] Field of Search ........................ 544/354; 514/349

[56] References Cited

U.S. PATENT DOCUMENTS 3,821,383 6/1974 Sestanj et al. .................. 514/296
4,209,527 6/1980 Sarges ............................ 548/305

FOREIGN PATENT DOCUMENTS 266102 5/1988 European Pat. Off. .

OTHER PUBLICATIONS

Sarges et al., Chemical Abstracts, vol. 110, No. 212764 (1989).

*Primary Examiner*—Anton S. Sutto
*Assistant Examiner*—E. Bernhardt
*Attorney, Agent, or Firm*—Peter C. Richardson; Paul H. Ginsburg

[57] ABSTRACT

A series of novel 4-arylsulfonyl-3,4-dihydro-2(1H)-quinoxalinone-1-alkanoic acid compounds have been prepared, including their lower alkyl ester derivatives, as well as the base salts of said acids with pharmacologically acceptable cations. These particular compounds are useful in therapy as agents for the control of certain chronic diabetic complications. Typical members include those compounds derived from 3,4-di-hydro-2-(1H)-quinoxalinone-1-acetic acid wherein an unsubstituted or substituted phenylsulfonyl moiety is located at the 4-position of the molecule. Ethyl 4-benzenesulfonyl-3,4-dihydro-2(1H)-quinoxalinone-1-acetate and 4-benzenesulfonyl-3,4-dihydro-2(1H)-quinoxalinone-1-acetic acid represent typical and preferred member compounds. Methods for preparing all these compounds from known starting materials are provided.

18 Claims, No Drawings

4-ARYLSULFONYL-3,4-DIHYDRO-2(1H)-QUINOXALINONE-1-ALKANOIC ACIDS, ESTERS, AND SALTS

TECHNICAL FIELD

This invention relates to new quinoxalinone derivatives of interest to those in the field of medicinal chemistry and chemotherapy. More particularly, it is concerned with a novel series of 4-substituted-3,4-dihydro-2(1H)-quinoxalinone-1-alkanoic acid compounds and their esters for the control of certain chronic complications arising from diabetes mellitus (e.g., diabetic cataracts, retinopathy and neuropathy).

BACKGROUND ART

Past attempts to obtain new and better oral antidiabetic agents have, for the most part, involved an endeavor to synthesize new compounds that lower blood sugar levels. More recently, several studies have been conducted concerning the effect of various organic compounds in preventing or arresting certain chronic complications of diabetes, such as diabetic cataracts, neuropathy and retinopathy, etc. For instance, K. Sestanj et al. in U.S. Pat. No. 3,821,383 discloses that certain aldose reductase inhibitors like 1,3-dioxo-1H-benz[d,e]isoquinoline-2(3H)-acetic acid and some closely-related derivatives thereof are useful for these purposes even though they are not known to be hypoglycemic. These compounds function by inhibiting the activity of the enzyme aldose reductase, which is primarily responsible for catalyzing the reduction of aldoses (like glucose and galactose) to the corresponding polyols (such as sorbitol and galactitol) in the human body. In this way, unwanted accumulations of galactitol in the lens of galactosemic subjects and or sorbitol in the lens, retina, peripheral nervous system and kidney of diabetic subjects are prevented or reduced. As a result, these compounds control certain chronic diabetic complications, including those of an ocular nature, since it is already known in the art that the presence of polyols in the lens of the eye leads to cataract formation and concomitant loss of lens clarity.

DISCLOSURE OF THE INVENTION

The present invention relates to novel 4-substituted-3,4-dihydro-2(1H)-quinoxalinone-1-alkanoic acid compounds useful as aldose reductase inhibitors for the control of certain chronic complications arising in a diabetic subject. It is also concerned with their corresponding esters which are useful for controlling the same diabetic complications, in addition to being useful as intermediates leading to the aforesaid aldose reductase inhibitor acids. More specifically, the novel compounds of this invention are selected from the group consisting of 4-arylsulfonyl-3,4-dihydro-2(1H)-quinoxalinone-1-alkanoic acids of the formula:

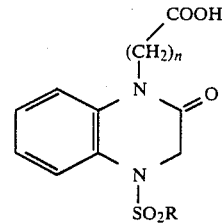

and the $C_1-C_6$ alkyl ester derivatives thereof, and the base salts of said acids with pharmacologically acceptable cations, wherein R is phenyl, hydroxyphenyl, fluorophenyl, chlorophenyl, dichlorophenyl, bromophenyl, $C_1-C_4$ alkylphenyl or $C_1-C_4$ alkoxyphenyl, and n is one or two. These novel compounds possess the ability to reduce or inhibit sorbitol formation in the lens and peripheral nerves of diabetic subjects.

One group of compounds of the present invention of particular interest is that wherein n is one and R is as previously defined, including their $C_1-C_6$ alkyl esters. Preferred compounds within this group include those where R is phenyl, p-fluorophenyl, p-chlorophenyl, 2,5-dichlorophenyl, o-tolyl, p-tolyl and o-anisyl, including their ethyl esters.

Another group of compounds of the present invention of interest is that of the aforesaid structural formula wherein n is two and R is as previously defined, including their $C_1-C_6$ alkyl esters. Preferred compounds within this group include the acid compound where R is phenyl and the ethyl ester derivative thereof.

Of special interest are such typical and preferred member compounds of the invention as ethyl 4-benzenesulfonyl-3,4-dihydro-2(1H)-quinoxalinone-1-acetate, ethyl 4-(p-fluorobenzenesulfonyl)-3,4-dihydro-2(1H)-quinoxalinone-1-acetate, ethyl 4-(p-chlorobenzenesulfonyl)-3,4-dihydro-2(1H)-quinoxalinone-1-acetate, ethyl 4-(2,5-dichlorobenzenesulfonyl)-3,4-dihydro-2(1H)-quinoxalinone-1-acetate, ethyl 4-(o-toluenesulfonyl)-3,4-dihydro-2(1H)-quinoxalinone-1-acetate, ethyl 4-(p-toluenesulfonyl)-3,4-dihydro-2(1H)-quinoxalinone-1acetate and ethyl 4-(p-methoxybenzenesulfonyl)-3,4-dihydro-2(1H)-quinoxalinone-1-acetate, including their corresponding parent carboxylic acids such as 4-benzenesulfonyl-3,4-dihydro-2(1H)-quinoxalinone-1-acetic acid, for example. These key compounds are particularly effective in lowering sorbitol levels in the sciatic nerve and lens of diabetic subjects. In addition, the esters are of value as intermediates leading to the production of the acids as will hereinafter be described.

Of these compounds, ethyl 4-benzenesulfonyl-3,4-dihydro-2(1H)-quinoxalinone-1-acetate and benzenesulfonyl-3,4-dihydro-2(1H)-quinoxalinone-1-acetic acid are most preferred. These two compounds both exhibit highly useful in vivo activity (i.e., suppression of sorbitol formation in the sciatic nerves of diabetic rats), with the activity of the ethyl ester being comparable to that of the aldose reductase inhibitor alrestatin, which is disclosed by K. Sestanj. et al. in aforesaid U.S. Pat. No. 3,821,383.

DETAILED DESCRIPTION

In accordance with the process employed for preparing the novel compounds of this invention, an appropriately substituted 4-arylsulfonyl-3,4-dihydro-2(1H)-quinoxalinone compound of the formula:

wherein R is as previously defined, is reacted with the appropriate lower alkanoic acid ester having the formula $X(CH_2)_nCOOR'$, where n is as earlier defined in the structural formula for the final products, X is either chlorine, bromine or iodine and R' is methyl or ethyl. This reaction is normally carried out in the presence of a basic condensing agent such as an alkali metal hydride, alkanolate or amide, or an alkali metal-alkyl or aryl compound, as the case may be, and is usually conducted in a reaction-inert polar organic solvent, preferably using a cyclic ether such as dioxane and tetrahydrofuran or one of the N,N-di-(lower alkyl)lower alkanoamides. Preferred solvents in this connection include dioxane, N,N-dimethylformamide N,N-di(n-propyl)formamide, N,N-dimethylacetamide, N,N-diethylacetamide, N,N-dimethylpropionamide and the like. In general, substantially equimolar amounts of reactant and reagent are employed (i.e., from about 0.80 to about 1.25 mole of halide reagent with respect to the 4-arylsulfonyl-3,4-dihydroquinoxlinone starting material) and the reaction is effected at a temperature that is in the range of from about 5° C. up to about 35° C. for a period of about seven up to about 64 hours. The reaction is usually conducted at room temperature (~20° C.) for a period of time that is ordinarily at least about seven and less than about 16 hours. The basic condensing agents required for the reaction are all selected from the class of alkali metal bases previously enumerated which are sufficiently strong to form salts with the weakly acidic 4-arylsulfonyl-3,4-dihydro-2(1H)-quinoxalinone and yet mild enough not to degrade the organic molecule under the conditions of the reaction. Such basic condensing agents include, for example, sodium hydride, lithium hydride and potassium hydride, etc., as well as sodium and potassium lower alkanolates like sodium methylate and potassium tert.-butoxide, as well as alkali metal amides like sodamide, lithium amide, potassium amide and so on. Upon completion of the reaction, the desired 4-arylsulfonyl-3,4-dihydro-2(1H)-quinoxalinone-1-alkanoic acid alkyl esters are readily recovered from the reaction mixture by the use of standard techniques well-known to those skilled in the art, e.g. the reaction mixture may be first diluted with water and then extracted with a suitable solvent such as ethyl acetate to ultimately afford the desired intermediate esters after first removing the solvent from the organic extract.

Conversion of the methyl or ethyl 4-arylsulfonyl-3,4-dihydro-2(1H)-quinoxalinone-1-alkanoic acid esters, prepared as described above, to the corresponding free acid final products of the present invention is then readily accomplished in a most convenient manner, viz., by effecting hydrolysis via the classical acid-catalyzed route, preferably using aqueous sulfuric acid in a lower alkanoic acid such as acetic acid at slightly elevated temperatures. In general, the acid-catalyzed hydrolysis reaction is effected at any temperature ranging from about 20° C. up to about 80° C. for a period of about 15 minutes to about 16 hours. Upon completion of the reaction, the desired 4-arylsulfonyl-3,4-dihydro-2(1H)-quinoxalinone-1-alkanoic acid final products are easily isolated from the reaction mixture by standard procedure, such as, for example, by concentration in vacuo, followed by extraction with a base and then acidification with a mineral acid to yield the desired compound in the form of a readily-recoverable precipitate. Further purification of the latter material, if desired, can then be carried out by means of crystallization from a suitable solvent system, preferably using a lower alkanol/hexane mixture.

Compounds of the invention wherein R of structural formula I is hydroxyphenyl can be readily prepared from the corresponding compounds where R is methoxy phenyl by simply dealkylating same in accordance with standard techniques well known to those skilled in the art. For instance, the use of boron tribromide readily converts 4-(p-methoxybenzenesulfonyl)-3,4-dihydro-2(1H)-quinoxalinone-1-acetic acid to the corresponding p-hydroxy compound. Moreover, certain compounds of the invention of structural formula I where R is alkoxyphenyl wherein said substituent is lower alkoxy of more than one carbon atom can alternatively be prepared from the corresponding methoxy compounds by first converting same to the corresponding hydroxy derivatives and then alkylating the latter with, for example, ethyl iodide or isopropyl bromide in a manner well known to those skilled in the art. As previously indicated, the 4-arylsulfonyl-3,4-dihydro-2(1H)-quinoxalinone-1-alkanoic acid final products (of structural formulae I) can be used as such for the therapeutic purposes of this invention or else simply converted to the corresponding lower alkyl ($C_1$-$C_6$) ester derivatives thereof in accordance with conventional techniques.

The lower alkyl esters of the 4-arylsulfonyl-3,4-dihydro-2(1H)-quinoxalinone-1-alkanoic acids of this invention are generally prepared by condensation of the acid with the appropriate alcohol in the presence of an acid catalyst in accordance with conventional organic procedure. This method offers a facile route to those particular esters which are not obtained in the first process step of the invention.

The 4-arylsulfonyl-3,4-dihydro-2(1H)-quinoxalinone starting materials (of structural formula II) required for preparing the methyl and ethyl 4-arylsulfonyl-3,4-dihydro-2(1H)-quinoxalinone-1-alkanoate esters in the first process step of this invention are all new compounds which are prepared by reacting 3,4-dihydro-2(1H)-quinoxalinone (3,4-dihydro-2-hydroxyquinoxaline), which is a known compound, with the appropriate arylsulfonyl chloride of choice in a base-catalyzed manner to form the desired arylsulfonyl derivative in accordance with the conventional methods of organic synthesis. This particular reaction is hereinafter described in detail in the experimental section of the specification (see Preparations A–G).

The chemical bases which are used as reagents in this invention to prepare the aforementioned pharmaceutically acceptable base salts are those which form non-toxic base salts with the herein described 4-arylsulfonyl-3,4-dihydro-2(1H)-quinoxalinone-1-alkanoic acid compounds such as 4-benzenesulfonyl-3,4-dihydro-2(1H)-quinoxalinone-1-acetic acid, for example. These particular non-toxic base salts include those derived from such pharmacologically acceptable cations as sodium, potassium, calcium and magnesium, etc. These salts can easily be prepared by simply treating the aforementioned 4-arylsulfonyl-3,4-dihydro-2(1H)-quinoxalinone-1- alkanoic acid compounds with an aqueous solution of the desired pharmacologically acceptable cation, and then evaporating the resulting solution to dryness, preferably under reduced pressure. Alternatively, they may be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

As previously indicated, the 4-arylsulfonyl-3,4-dihydro-2(1H)-quinoxalinone-1-alkanoic acid compounds of this invention, including their esters, are readily adapted to therapeutic use as agents for the control of chronic diabetic complications, in view of their ability to reduce sorbitol levels in diabetic subjects to a statistically significant degree. For instance, ethyl 4-benzenesulfonyl-3,4-dihydro-2(1H)-quinoxalinone-1-acetate, a typical and preferred agent of the present invention, has been found to inhibit the formation of sorbitol levels in diabetic rats to a significantly high degree when given by the intraperitoneal route of administration at a dose level of 100 mg./kg. Furthermore, the herein described compounds of this invention can be administered by either the oral, topical or parenteral routes of administration. In general, these compounds are ordinarily administered in dosages ranging from about 1.0 mg. to about 200 mg. per kg. of body weight per day, although variations will necessarily occur depending upon the weight and condition of the subject being treated and the particular route of administration chosen.

These compounds may be administered either alone or in combination with pharmaceutically acceptable carriers by any of the routes previously indicated, and such administration can be carried out in either single or multiple dosages. More particularly, the compounds of this invention can be administered in a wide variety of different dosage forms, i.e., they may be combined with various pharmaceutically-acceptable inert carriers in the form of tablets, capsules, lozenges, troches, hard candies, powders, sprays, aqueous suspensions, injectable solutions, elixirs, syrups, and the like. Such carriers include solid diluents or fillers, sterile aqueous media and various non-toxic organic solvents. In general, the compounds of the invention will be present in such dosage forms at concentration levels ranging from about 0.5% to about 90% by weight of the total composition to provide the desired unit dosage.

For oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include the high molecular weight polyethylene glycols. When aqueous suspensions and/or elixirs are desired for oral administration, the essential active ingredient therein may be combined with various sweetening or flavoring agents, coloring matter or dyes, and if so desired emulsifying and/or suspending agents as well, together with such diluents as water, ethanol, propylene, glycol, glycerin and various combinations thereof.

For parenteral administration, solutions of these 4-arylsulfonyl-3,4-dihydro-2(1H)-quinoxalinone-1-alkanoic acids or their esters in sesame or peanut oil or in aqueous propylene glycol or N,N-dimethylformamide may be employed, as well as sterile aqueous solutions of the corresponding water-soluble, alkali metal or alkaline-earth metal salts previously enumerated. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal injection. In this connection, the sterile aqueous media employed are all readily obtainable by standard techniques well-known to those skilled in the art. Additionally, it is also possible to administer the aforesaid 4-arylsulfonyl-3,4-dihydro-2(1H)-quinoxalinone-1-alkanoic acid compounds and their esters topically via an appropriate ophthalmic solution (0.5-2.0%) applied dropwise to the eye.

The activity of the compounds of the present invention, as agents for the control of chronic diabetic complications, is determined by their ability to successfully pass one or two of the following standard biological or pharmacological tests, viz., (1) measuring their ability to inhibit the enzyme activity of isolated aldose reductase, and (2) measuring their ability to reduce or inhibit sorbitol accumulation in the sciatic nerve of acutely streptozotocinized (i.e., diabetic) rats.

PREPARATION A

A suspension of 10 g. (0.068 mole) of 3,4-dihydro-2(1H)-quinoxalinone (3,4-dihydro-2-hydroxyquinoxaline) [prepared in 50% yield according to the procedure described by W. H. Perkin et al. in the *Journal of the Chemical Society*, Vol. 123, p.2399(1923)] and 9.6 g. (0.069 mole) of potassium carbonate in 250 ml. of acetone was stirred under a nitrogen atmosphere at 40° C., while 11.5 g. (0.07 mole) of benzenesulfonyl chloride was added during the course of a 30-minute period. The reaction mixture was next heated at reflux temperature for 14 hours and then poured onto 500 ml. of ice. The resulting brown solid was recrystallized from ethyl acetate to yield 10.2 g (52%) of pure 4-benzenesulfonyl-3,4-dihydro-2(1H)-quinoxalinone, m.p. 183°-185° C. The pure product was further characterized by means of nuclear magnetic resonance data and elemental analysis.

Anal. Calcd. for $C_{14}H_{12}N_2O_3S$: C, 58.32; H, 4.19, N, 9.72. Found: C, 58.36; H, 4.37; N, 9.58.

PREPARATION B

A suspension of 4.0 g. (0.027 mole) of 3,4-dihydro-2(1H)-quinoxalinone and 4.0 g. (0.029 mole) of potassium carbonate in 100 ml. of acetone stirred under a nitrogen atmosphere at room temperature (~20° C.), while 6.67 g. (0.035 mole) of o-toluenesulfonyl chloride was slowly added thereto in a dropwise manner. The reaction mixture was then stirred at room temperature for a period of approximately 71 hours prior to the work-up. The latter was accomplished by concentrating the mixture in vacuo, dissolving the residue in ethyl acetate, washing with 1N hydrochloric acid, drying over anhydrous magnesium sulfate and treating the dried organic filtrate with activated charcoal. The clear filtrate thus obtained (i.e., after filtration) was then concentrated in vacuo to yield the desired solid product. Recrystallization of the latter material from ethyl acetate/hexane (twice) then gave 1.06 g. (20%) of pure 4-(o-toluenesulfonyl)-3,4-dihydro-2(1H)-quinoxalinone, m.p. 149°–151° C.

Anal. Calcd. for $C_{15}H_{14}N_2O_3S$: C, 59.58; H, 4.67; N, 9.27. Found: C, 59.63; H, 4.71; N, 9.15.

PREPARATION C

A solution consisting of 4.0 g. (0.027 mole) of 3,4-dihydro-2(1H)-quinoxalinone dissolved in 100 ml. of chloroform containing 2.73 g. (0.027 mole) of triethylamine (3.74 ml.) was stirred in a 250 ml. flask under a dry nitrogen atmosphere at room temperature (~20° C.), while 5.84 g. (0.03 mole) of p-fluorobenzenesulfonyl chloride dissolved in 100 ml. of chloroform was slowly added thereto in a dropwise manner. The reaction mixture was then stirred at this point for a period of approximately 64 hours, and finally poured into 300 ml. of water. Extraction of the aqueous mixture with chloroform, followed by evaporation of the solvent under reduced pressure then gave a solid residue, which was subsequently dissolved in ethyl acetate and washed with 1N hydrochloric acid. The washed ethyl acetate solution was thereafter concentrated in vacuo, and the residual solid material was recrystallized from ethyl acetate/hexane (twice) to yield 2.81 g. (37%) of pure 4-(p-fluorobenzenesulfonyl)-3,4-dihydro-2(1H)-quinoxalinone, m.p. 176°–178° C.

Anal. Calcd. for $C_{14}H_{11}FN_2O_3S$: C, 54.89; H, 3.62; N, 9.15. Found: C, 54.93; H, 3.59; N, 8.79.

PREPARATION D

A solution consisting of 6.7 g. (0.045 mole) of 3,4-dihydro-2(1H)-quinoxalinone dissolved in 150 ml. of chloroform containing 10.1 g.(0.10 mole) of triethylamine (14 ml.) was stirred in a flask under a nitrogen atmosphere at room temperature (~20° C.), while 10.6 g. (0.05 mole) of p-chlorobenzenesulfonyl chloride dissolved in 150 ml. of chloroform was slowly added thereto in a dropwise manner. The reaction mixture was next stirred at this point for a period of seven hours, another equivalent of p-chlorobenzenesulfonyl chloride was added to the mixture and stirring was continued for approximately 16 more hours (i.e., overnight). Upon completion of this step, the reaction mixture was evaporated to dryness under reduced pressure and the resulting residue dissolved in water, extracted with ethyl acetate and dried over anhydrous magnesium sulfate. After removal of the drying agent by means of filtration, the resulting filtrate was concentrated in vacuo and the residual material was subsequently dissolved in ethyl acetate, washed with 1N hydrochloric acid and dried over anhydrous magnesium sulfate. The dried organic filtrate was then treated with activated charcoal, filtered again and the clear filtrate thus obtained was concentrated in vacuo to yield the desired crystalline product. Recrystallization of the latter material from ethyl acetate/hexane (twice) then gave 3.97 g. (27%) of pure 4-(p-chlorobenzenesulfonyl)-3,4-dihydro-2(1H)-quinoxalinone, m.p. 213°–215° C. A further recrystallization raised the melting point to 215°–217° C.

Anal Calcd. for $C_{14}H_{11}ClN_2O_3S$: C, 52.09; H, 3.44; N, 8.67. Found: C, 52.23; H, 3.37; N, 8.63.

PREPARATION E

A solution consisting of 4.0 g. (0.027 mole) of 3,4-dihydro-2(1H)-quinoxalinone dissolved in 35 ml. of glacial acetic acid was heated on a steam bath and treated with 6.48 g. (0.034 mole) of p-toluenesulfonyl chloride, followed by the addition of 2.8 g. (0.034 mole) of sodium acetate thereto. The sodium acetate was successively added in one-half, one-quarter, one-eighth and one-eighth equivalent portions (i.e., in 0.0135, 0.007, 0.0035 and 0.0035 molar portions), followed by a final one-quarter equivalent (0.007 mole) portion. The reaction mixture was next allowed to heat for a period of ten minutes after each addition and for 15 minutes after the final addition. Upon completion of this step, the mixture was vigorously stirred while water (ca. 300 ml.) was rapidly added thereto in order to effect precipitation. The crystals which formed were then collected by means of suction filtration and successively washed with separate portions of 60% acetic acid, 6N hydrochloric acid and water, followed by drying in a dessicator overnight for a period of approximately 16 hours. The product so obtained was recrystallized from ethanol and some water to afford 4.85 g. (60%) of pure 4-(p-toluenesulfonyl)-3,4-dihydro-2(1H)-quinoxalinone, m.p. 189°–191° C.

Anal. Calcd. for $C_{15}H_{14}N_2O_3S$: C, 59.58; H, 4.67; N, 9.27. Found: C, 59.67; H, 4.58; N, 9.23.

PREPARATION F

A solution consisting of 4.0 g. (0.027 mole) of 3,4-dihydro-2(1H)-quinoxalinone dissolved in 50 ml. of glacial acetic acid was heated on a steam bath and treated with 7.03 g. (0.0034 mole) of p-methoxybenzenesulfonyl chloride, followed by the addition of 2.8 g. (0.034 mole) of sodium acetate thereto. The sodium acetate was successively added in 0.0135, 0.007, 0.0035 and 0.0035 molar portions, with a 15-minute heating period allowed between each addition. A final 0.007 mole portion of sodium acetate was then added and an additional 15-minute heating period was allowed. Upon completion of this step, the resulting reaction mixture was poured into 450 ml. of water and stirred until ambient temperatures were attained. At this point, the product was recovered by means of filtration, washed with 60% aqueous acetic acid and water, and air-dried to constant weight (yield, 7.5 g.). Recrystallization of the latter material from aqueous ethanol then gave 7.0 g. (81%) of pure 4-(p-methoxybenzenesulfonyl)-3,4-dihydro-2(1H)-quinoxalinone, m.p. 164°–166° C. A further recrystallization from ethyl acetate/hexane raised the melting point to 180°–182° C.

Anal. Calcd. for $C_{15}H_{14}N_2O_4S$: C, 56.59; H, 4.43; N, 8.80. Found C, 56.82; H, 4.36; N, 8.58.

PREPARATION G

A solution consisting of 7.0 g. (0.047 mole) of 3,4-dihydro-2(1H)-quinoxalinone dissolved in 50 ml. of glacial acetic acid was heated to 100° C. and treated with 14.5 g. (0.059 mole) of 2,5-dichlorobenzenesulfonyl chloride. The resulting solution was then brought to the boiling point, followed by the addition of 4.7 g. (0.059 mole) of sodium acetate thereto. The sodium acetate was successively added in 0.024, 0.011, 0.006, 0.006 and 0.011 molar portions, with a 15-minute heating period allowed between each addition. A final 0.011 mole portion of sodium acetate was then added and an additional 30-minute heating period was allowed. Upon completion of this step, the resulting reaction mixture was poured into 500 ml. of water and cooled to room temperature (~20° C.) with stirring. At this point, the product was recovered by means of filtration and then dissolved in ethyl acetate, followed by washing of the latter organic solution with 5N hydrochloric acid and drying over anhydrous magnesium sulfate. After removal of the drying agent by means of filtration and part of the solvent by means of evaporation under reduced pressure, the concentrate yielded a crystalline residual material that was subsequently recrystallized from aqueous ethanol to afford 2.9 g. (17%) of pure 4-(2,5-dichlorobenzenesulfonyl)-3,4-dihydro-2(1H)-quinoxalinone, m.p. 228°–230° C.

Anal. Calcd. for $C_{14}H_{10}Cl_2N_2O_3S$: C, 47.07; H, 2.82; N, 7.84. Found: C, 46.83; H, 2.85; N, 7.68.

EXAMPLE 1

A suspension of 192 mg. (0.004 mole) of 50% sodium hydride in 15 ml. of dioxane in a dry flask under a nitrogen atmosphere was treated with 1 g. (0.0035 mole) of 4-benzenesulfonyl-3,4-dihydro-2(1H)-quinoxalinone (the product of Preparation A) in 20 ml. of dioxane and then with 688 mg. (0.004 mole) of ethyl bromoacetate during the course of 15-minute period. The resulting reaction mixture was stirred at room temperature (~20° C.) for a period of seven hours, poured onto 400 ml. of ice, and the precipitated solid product was recrystallized from carbon tetrachloride to yield 844 mg. (65%) of pure ethyl 4-benzenesulfonyl-3,4-dihydro-2(1H)-quinoxalinone-1-acetate, m.p. 113°–115° C. The pure product was further characterized by means of nuclear magnetic resonance data and elemental analysis.

Anal. Calcd. for $C_{18}H_{18}N_2O_5S$: C, 57.74; H, 4.85; N, 7.48. Found: C, 57.39; H, 4.88; N, 4.72.

EXAMPLE 2

A suspension of 336 mg. (0.007 mole) of 50% sodium hydride in 20 ml. of dioxane in a dry flask under a nitrogen atmosphere was treated with 1.8 g. (0.006 mole) of 4-(o-toluenesulfonyl)-3,4-dihydro-3,4-dihydro-2(1H)-quinoxalinone (the product of Preparation B) dissolved in 40 ml. of dioxane (added slowly with stirring to prevent foaming) and then with 1.17 g. (0.007 mole) of ethyl bromoacetate (0.81 ml.) dissolved in 10 ml. of dioxane, which was added slowly in a dropwise manner with stirring. The reaction mixture was next stirred at room temperature (~20° C.) for a period of approximately 16 hours (i.e., overnight) prior to the work-up. The latter was accomplished by concentrating the mixture in vacuo dissolving the residue in water, extracting with ethyl acetate, drying over anhydrous magnesium sulfate and treating the dried organic filtrate with activated charcoal. The clear filtrate thus obtained (i.e., after filtration) was then concentrated in vacuo to yield the desired crystalline product. Recrystallization of the latter material from diethyl ether/hexane then gave 262 mg. (11%) of pure ethyl 4-(o-toluenesulfonyl)-3,4-dihydro-2(1H)-quinoxalinone-1-acetate, m.p. 113°–115° C.

Anal. Calcd. for $C_{19}H_{20}N_2O_5S$: C, 58.74; H, 5.19; N, 7.21. Found: C, 58.93; H, 5.17; N, 6.96.

EXAMPLE 3

A stirred suspension of 960 mg. (0.020 mole) of 50% sodium hydride in 20 ml. of dioxane in a dry flask under a nitrogen atmosphere was treated with 5.3 g. (0.017 mole) of 4-(p-fluorobenzenesulfonyl)-3,4-dihydro-2(1H)-quinoxalinone (the product of Preparation C) suspended in 100 ml of dioxane (added slowly to prevent foaming) and then with 3.34 g. (0.020 mole) of ethyl bromcacetate (2.3 ml.) diluted with 20 ml. of dioxane, which was added in a dropwise fashion. The reaction mixture was next stirred at room temperature (~20° C.) for a period of approximately 16 hours (i.e., overnight) prior to the work-up. The latter was accomplished by concentrating the mixture in vacuo, dissolving the residue in water, extracting with ethyl acetate, drying over anhydrous magnesium sulfate and concentrating the dried organic filtrate, followed by treatment with carbon tetrachloride so as to induce crystallization. Recrystallization of the thus obtained solid material from carbon tetrachloride and then from diethyl ether/hexane gave a crude product, which was subsequently washed several times with 5N hydrochloric acid after having first been dissolved in diethyl ether. The washed product was then chromatographed on a silica gel column, using benzene containing 1% glacial acetic acid as the eluant. The first ten fractions were combined and subsequently concentrated in vacuo, followed by a rinse with hexane to remove excess acetic acid. The washed concentrate was then scratched under hexane to induce crystallization, and the crystalline product obtained in this manner was thereafter recrystallized from ethyl acetate/hexane to yield 420 mg. (6%) of pure ethyl 4-(p-fluorobenzenesulfonyl)-3,4-dihydro-2(1H)-quinoxalinone-1-acetate, m.p. 94°–96° C.

Anal. Calcd. for $C_{18}H_{17}FN_2O_5S$ C, 55.09; H, 4.37; N, 7.14. Found C, 55.25; H, 4.46; N, 7.13.

EXAMPLE 4

A suspension of 700 mg. (0.0145 mole) of 50% sodium hydride in 25 ml. of dioxane in a dry flask under a nitrogen atmosphere was treated with 4.0 g. (0.012 mole) of 4-(p-chlorobenzenesulfonyl)-3,4-dihydro-2(1H)-quinoxalinone (the product of Preparation D) suspended in 150 ml. of dioxane (added slowly with stirring to prevent foaming) and then with 2.42 g. (0.0145 mole) of ethyl bromoacetate (1.67 ml.) diluted with 20 ml. of dioxane, which was added slowly in a dropwise manner with stirring. The reaction mixture was next stirred at room temperature (~20° C.) for a period of approximately 16 hours (i.e., overnight) prior to the workup. The latter was accomplished by concentrating the mixture in vacuo, dissolving the residue in water, extracting with ethyl acetate, drying over anhydrous magnesium sulfate and concentrating the dried organic filtrate. The oily gummy substance which resulted was then chromatographed on a silica gel column, using benzene containing 1% glacial acetic acid as the eluant. Fraction Nos. 8-20 containing the product were combined and these were subsequently concentrated in vacuo, followed by a rinse with diethyl ether/hexane to remove excess acetic acid. The washed concentrate was then scratched under hexane to induce crystallization, and the crystalline product obtained in this manner was thereafter recrystallized from ethyl acetate/hexane to yield 560 mg. (11%) of pure ethyl 4-(p-chlorobenzenesulfonyl)-3,4-dihydro-2(1H)-quinoxalinone-1-acetate, m.p. 97°–99° C.

Anal Calcd. for $C_{18}H_{17}ClN_2O_5S$: C, 52.87; H, 4.19; N, 6.85. Found: C, 53.18; H, 4.11; N, 7.09.

EXAMPLE 5

A stirred suspension of 576 mg. (0.012 mole) of 50% sodium hydride in 25 ml. of dioxane in a dry flask under a nitrogen atmosphere was treated with 3.0 g. (0.01 mole) of 4-(p-toluenesulfonyl)-3,4-dihydro-2(1H)-quinoxalinone (the product of Preparation E) dissolved in 25 ml. of dioxane (added slowly to prevent foaming) and then with 2.00 g. (0.012 mole) of ethyl bromoacetate (1.38 ml.) diluted with 15 ml. of dioxane, which was added slowly in a dropwise manner. The reaction mixture was next stirred at room temperature (~20° C.) for a period of approximately 16 hours (i.e., overnight) prior to the work-up. The latter was accomplished by concentrating the mixture in vacuo, dissolving the residue in water, extracting with ethyl acetate, drying over anhydrous magnesium sulfate and treating the dried organic filtrate with activated charcoal. The clear filtrate thus obtained (i.e., after filtration) was then concentrated in vacuo to yield crystals of the desired final product. Recrystallization of the latter material from diethyl ether/hexane then gave 291 mg. (8%) of pure ethyl 4-(p-toluenesulfonyl)-3,4-dihydro-2(1H)-quinoxalinone-1-acetate, m.p. 105°–108° C.

Anal. Calcd. for $C_{19}H_{20}N_2O_5S$: C, 58.74; H, 5.19; N, 7.21. Found: C, 58.59; H, 5.16; N, 7.31.

EXAMPLE 6

A stirred suspension of 720 mg. (0.015 mole) of 50% sodium hydride in 30 ml. of dioxane in a dry flask under a nitrogen atmosphere was treated with 4.0 g. (0.013 mole) of 4-(p-methoxybenzenesulfonyl)-3,4-dihydro-2(1H)-quinoxalinone (the product of Preparation F) dissolved in 55 ml. of dioxane (added slowly to prevent foaming) and then with 2.5 g. (0.015 mole) of ethyl bromoacetate (1.7 ml.) diluted with 15 ml. of dioxane, which was added slowly in a dropwise manner. The reaction mixture was next stirred at room temperature (~20° C.) for a period of approximately 64 hours prior to the work-up. The latter was accomplished by concentrating the mixture in vacuo, dissolving the residue in water, extracting with ethyl acetate, drying over anhydrous magnesium sulfate and concentrating the dried organic filtrate. The gummy substance which resulted after evaporation of the solvent was crystallized under diethyl ether to give 2.16 g. of crude product melting at 107°–109° C. Recrystallization of the latter material from ethyl acetate/hexane then gave 1.46 g. (29%) of pure ethyl 4-(p-methoxybenzenesulfonyl)-3,4-dihydro-2(1H)-quinoxalinone-1-acetate, m.p. 118°–120° C.

Anal. Calcd. for $C_{19}H_{20}N_2O_6S$: C, 56.42; H, 4.98; N, 6.93. Found: C, 56.62; H, 4.99; N, 6.80.

EXAMPLE 7

A stirred suspension of 600 mg. (0.0125 mole) of 50% sodium hydride in 25 ml. of dioxane in a dry flask under a nitrogen atmosphere was treated with 3.8 g. (0.01 mole) of 4-(2,5-dichlorobenzenesulfonyl)-2(1H)-quinoxalinone (the product of Preparation G) dissolved in 75 ml. of dioxane (added slowly to prevent foaming) and then with 2.1 g. (0.0125 mole) of ethyl bromoacetate (1.4 ml.) diluted with 20 ml. of dioxane, which was added slowly in a dropwise manner. The reaction mixture was next stirred at room temperature (~20° C.) for a period of approximately 64 hours prior to the work-up. The latter was accomplished by concentrating the mixture in vacuo, dissolving the residue in water, extracting with ethyl acetate and concentrating the organic extract, followed by crystallization of the residue under carbon tetrachloride to yield 1.75 g. of crude product melting at 132.5°–135° C. Recrystallization of the latter material from carbon tetrachloride (twice) then gave 910 mg. (19%) of pure ethyl 4-(2,5-dichlorobenzenesulfonyl)-3,4-dihydro-2(1H)-quinoxalinone-1-acetate, m.p. 134°–136° C.

Anal. Calcd. for $C_{18}H_{16}Cl_2N_2O_5S$: C, 48.76; H, 3.64; N, 6.32. Found C, 48.66; H, 3.59; N, 6.23.

EXAMPLE 8

A suspension of 3 g. (0.008 mole) of ethyl 4-benzenesulfonyl-3,4-dihydro-2(1H)-quinoxalinone-1-acetate in 30 ml. of 30% aqueous sulfuric acid and 20 ml. of 98% acetic acid was heated to 80° C. for a period of 15 minutes, then at 60° C. for a period of five hours and finally kept at room temperature (~20° C.) for a period of 16 hours. The resulting solution was then concentrated under reduced pressure to an oil, which was subsequently dissolved in saturated aqueous sodium bicarbonate solution and thereafter treated with 3N hydrochloric acid to give a precipitate. The solid product was recovered by means of filtration and then recrystallized from ethanol/petroleum ether after treatment with activated charcoal to yield 750 mg. (27%) of pure 4-benzenesulfonyl-3,4-dihydro-2(1H)-quinoxalinone-1-acetic acid, m.p. 122° C. (decomp.). The pure product was further characterized by means of nuclear magnetic resonance data and elemental analysis.

Anal. Calcd. for $C_{16}H_{14}N_2O_5S \cdot 0.25H_2O$: C, 54.77; H, 4.17; N, 7.98. Found C, 54.83; H, 4.44; N, 7.97.

EXAMPLE 9

The procedure described in Example 8 is repeated except that ethyl 4-(o-toluenesulfonyl)-3,4-dihydro-2(1H)-quinoxalinone-1-acetate (the product of Example 2) was the starting material employed in place of ethyl 4-benzenesulfonyl-3,4-dihydro-2(1H)-quinoxalinone-1-acetate, using the same molar portions as before. In this particular case, the corresponding final product obtained is 4-(o-toluenesulfonyl)-3,4-dihydro-2(1H)-quinoxalinone-1-acetic acid.

EXAMPLE 10

The procedure described in Example 8 was repeated except that ethyl 4-(p-fluorobenzenesulfonyl)-3,4-dihydro-2(1H)-quinoxalinone-1-acetate (the product of Example 3) was the starting material employed in place of ethyl 4-benzenesulfonyl-3,4-dihydro-2(1H)-quinoxalinone-1-acetate, using the same molar proportions as before. In this particular case, the corresponding final product obtained is 4-(p-fluorobenzenesulfonyl)-3,4-dihydro-2(1H)-quinoxalone-1-acetic acid.

EXAMPLE 11

The procedure described in Example 8 is repeated except that ethyl 4-(p-chlorobenzenesulfonyl)-3,4-dihydro-2(1H)-quinoxalinone-1-acetate is the starting material employed in place of ethyl 4-benzenesulfonyl-3,4-dihydro-2(1H)-quinoxalone-1-acetate, using the same molar proportions as before. In this particular case, the corresponding final product obtained is 4-(p-chlorobenzenesulfonyl)-3,4-dihydro-2(1H)-quinoxalone-1-acetic acid.

EXAMPLE 12

The procedure described in Example 8 is repeated except that ethyl 4-(p-toluenesulfonyl)-3,4-dihydro-2(1H)-quinoxalinone-1-acetate is the starting material employed in place of ethyl 4-benzenesulfonyl-3,4-dihydro-2(1H)-quinoxalinone acetate, using the same molar proportions as before. In this particular case, the corresponding final product obtained is 4-(p-toluenesulfonyl)-3,4-dihydro-2(1H)-quinoxalinone-1-acetic acid.

EXAMPLE 13

The procedure described in Example 8 is repeated except that ethyl 4-(p-methoxybenzenesulfonyl)-3,4-dihydro-2(1H)-quinoxalinone-1-acetate is the starting material employed in place of ethyl 4-benzenesulfonyl-3,4-dihydro-2(1H)-quinoxalinone-1-acetate, using the same molar proportions as before. In this particular case, the corresponding final product obtained is 4-(p-methoxybenzenesulfonyl)-3,4-dihydro-2(1H)-quinoxalinone-1-acetic acid.

EXAMPLE 14

The procedure described in Example 8 is repeated except that ethyl 4-(2,5-dichlorobenzenesulfonyl)-3,4-dihydro-2(1H)-quinoxalinone-1-acetate is the starting material employed in place of ethyl 4-benzenesulfonyl-3,4-dihydro-2(1H)-quinoxalinone-1-acetate, using the same molar proportions as before. In this particular case, the corresponding final product obtained is 4-(2,5-dichlorobenzenesulfonyl)-3,4-dihydro-2(1H)-quinoxalinone-1-acetic acid.

I claim:

1. A 4-arylsulfonyl-3,4-dihydro-2(1H)-quinoxalinone-1-alkanoic acid compound of the formula:

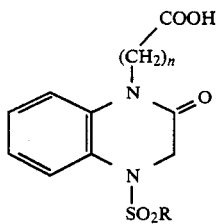

or a $C_1$–$C_6$ alkyl ester derivative thereof, or a base salt of said acid with a pharmacologically acceptable cation, wherein R is phenyl, hydroxyphenyl, fluorophenyl, chlorophenyl, dichlorophenyl, bromophenyl, $C_1$–$C_4$ alkylphenyl or $C_1$–$C_4$ alkoxyphenyl; and n is one or two.

2. A compound as claimed in claim 1 wherein n is two.

3. A compound as claimed in claim 1 wherein n is one.

4. A compound as claimed in claim 2 wherein R is phenyl.

5. A compound as claimed in claim 3 wherein R is phenyl.

6. A compound as claimed in claim 3 wherein R is fluorophenyl.

7. A compound as claimed in claim 3 wherein R is chlorophenyl.

8. A compound as claimed in claim 3 wherein R is dichlorophenyl.

9. A compound as claimed in claim 3 wherein R is $C_1$–$C_4$ alkylphenyl

10. A compound as claimed in claim 9 wherein R is tolyl.

11. A compound as claimed in claim 3 wherein R is $C_1$–$C_4$ alkoxyphenyl.

12. A compound as claimed in claim 11 wherein R is anisyl.

13. A compound as claimed in claim 1 which is a $C_1$–$C_6$ alkyl ester.

14. A compound as claimed in claim 3 which is an ethyl ester.

15. Ethyl 4-benzenesulfonyl-3,4-dihydro-2(1H)-quinoxalinone-1-acetate.

16. 4-Benzenesulfonyl-3,4-dihydro-2(1H)-quinoxalinone-1-acetic acid.

17. A pharmaceutical composition suitable for oral, topical or parenteral administration comprising a pharmaceutically acceptable carrier and a compound as claimed in claim 1 in an amount effective for the treatment of diabetes-associated chronic complications.

18. A method for treating a diabetic subject to prevent or alleviate chronic complications arising in said subject, which comprises administering to said diabetic subject an effective amount of a compound as claimed in claim 1.

* * * * *